United States Patent [19]
Sterzer et al.

[11] Patent Number: 5,688,050
[45] Date of Patent: Nov. 18, 1997

[54] TEMPERATURE-MEASURING MICROWAVE RADIOMETER APPARATUS

[75] Inventors: Fred Sterzer, Princeton; Daniel D. Mawhinney, Livingston, both of N.J.

[73] Assignee: MMTC, Inc., Princeton, N.J.

[21] Appl. No.: 415,302

[22] Filed: Apr. 3, 1995

[51] Int. Cl.$^6$ .................................................. G01J 5/00
[52] U.S. Cl. ............................ 374/122; 374/121; 374/129
[58] Field of Search ..................................... 374/122, 121, 374/120, 129, 175

[56] References Cited

U.S. PATENT DOCUMENTS

| | | | |
|---|---|---|---|
| 3,777,270 | 12/1973 | Hardy et al. | 374/122 |
| 4,190,053 | 2/1980 | Sterzer | 374/122 |
| 4,235,107 | 11/1980 | Ludeke et al. | 374/122 |
| 5,149,198 | 9/1992 | Sterzer | 374/139 |
| 5,176,146 | 1/1993 | Maurice et al. | 374/122 |

OTHER PUBLICATIONS

Sterzer, "Microwave Radiometers for Non-invasive Measurements of Subsurface Tissue Temperatures", Automedica, 1987, vol. 8. pp. 203–211.
Ludeke et al, "Microwave Radiometric System for Biomedical True Temperature and Emissivity Measurements", Journal of Microwave Power, 18(3), 1983, pp. 277–283.

*Primary Examiner*—Daniel G. DePumpo
*Attorney, Agent, or Firm*—George J. Seligsohn

[57] ABSTRACT

Disclosed are four improvements in temperature-measuring radiometric equipment. The first improvement is directed to increasing the sensitivity of a radiometer by employing microwave noise power derived from a reference noise source in an amount that corresponds to a temperature higher than that of the specimen, and applying the reference-noise-source-derived microwave noise power as an input to the radiometer for a shorter time than is microwave noise power derived from a specimen. The second improvement is directed to reducing emissivity error by employing open-loop means comprising a microwave circulator for applying microwave noise power generated by at least one resistor thermostatically heated to a temperature in the neighborhood of the temperature of a patient's body tissue back to the body tissue. The third improvement, which is suitable for use in an applicator insertable into a natural opening of a patient's body that is employed in the detection and location of a cancerous lesion, is directed to a microwave radiometer that employs two displaced microwave antennas to measure the temperature difference between two points of a patient's body tissue or other type of specimen. The fourth improvement is directed to radiometric equipment that is combined with mammographic equipment to provide a superior capability for detecting and locating a breast cancer lesion.

15 Claims, 14 Drawing Sheets

TEMPERATURE-MEASURING MICROWAVE RADIOMETER APPARATUS

BACKGROUND OF THE INVENTION

1. Field of the Invention

This invention relates to apparatus employing a microwave radiometer to measure the temperature of a specimen and, more particularly, to improvements in such apparatus.

2. Description of the Prior Art

Apparatus employing a microwave radiometer to measure the temperature of a specimen has been known in the art for some time and, by way of example, is used medically to measure the subsurface body tissue temperature, of a patient. In this regard, reference is made to the article "Microwave Radiometers for Non-invasive Measurements of Subsurface Tissue Temperatures", by F. Sterzer, which appears in the publication *Automedica*, 1987, Vol. 8, pages 203–211. Reference is also made to the article "Microwave Radiometric System for Biomedical 'True Temperature' and Emissivity Measurements", by K. M. Lüdeke and J. Köhler, which appears in the publication *Journal of Microwave Power*, 18(3), 1983, pages 277–283.

More recently, several improvements in apparatus employing a microwave radiometer to measure the temperature of a specimen have been made, which improvements are disclosed in U.S. Pat. No. 5,149,198, that issued Sep. 22, 1992 and is assigned to the same assignee as the present invention. The disclosure of U.S. Pat. No. 5,149,198 is incorporated herein by reference.

The present invention is directed to additional improvements in apparatus employing a microwave radiometer to measure the temperature of a specimen, including improvements to the microwave radiometer itself.

SUMMARY OF THE INVENTION

In accordance with a first improvement to apparatus employing a microwave radiometer to measure the temperature of a specimen, radiometer sensitivity is increased by employing microwave noise power derived from a reference noise source in an amount that corresponds to a temperature higher than that of the specimen is applied as an input to the radiometer for a shorter time than is microwave noise power from the specimen.

In accordance with a second improvement to apparatus employing a microwave radiometer to measure the temperature of patient's body tissue, emissivity error is reduced by employing open-loop means comprising a microwave circulator for applying microwave noise power generated by at least one resistor thermostatically heated to a temperature in the neighborhood of the temperature of a patient's body tissue back to the body tissue.

In accordance with a third improvement, which is suitable for use with a standard external applicator as well as for use in an applicator insertable into a natural opening of a patient's body that is employed in the detection and location of a cancerous lesion, a microwave radiometer employs two displaced microwave antennas to measure the temperature difference between two points of a patient's body tissue or other type of specimen.

In accordance with a fourth improvement, radiometric equipment is combined with mammographic equipment to provide a superior capability for detecting and locating a breast cancer lesion.

DESCRIPTION OF THE PREFERRED EMBODIMENTS

As known in the art and disclosed in the aforesaid U.S. Pat. No. 5,149,198, a specimen emits electromagnetic radiation that has an intensity and a frequency-spectrum distribution each of which is a function of the temperature of the specimen and the characteristics of the material of which the specimen is composed. This frequency-spectrum distribution includes a microwave interval including a portion to which a microwave antenna means is responsive. The temperature of the specimen is sensed by such microwave antenna means being positioned in cooperative spatial relationship with the specimen to receive that portion of the electromagnetic radiation therefrom which is within this microwave interval. A microwave radiometer then compares the relative intensity of the microwave noise output from the microwave antenna means with respect to the intensity of the output from a calibrated reference microwave noise source. The temperature of the specimen may be indicated by a temperature meter in response to the output from the microwave receiver applied as an input thereto.

Figure 1A:
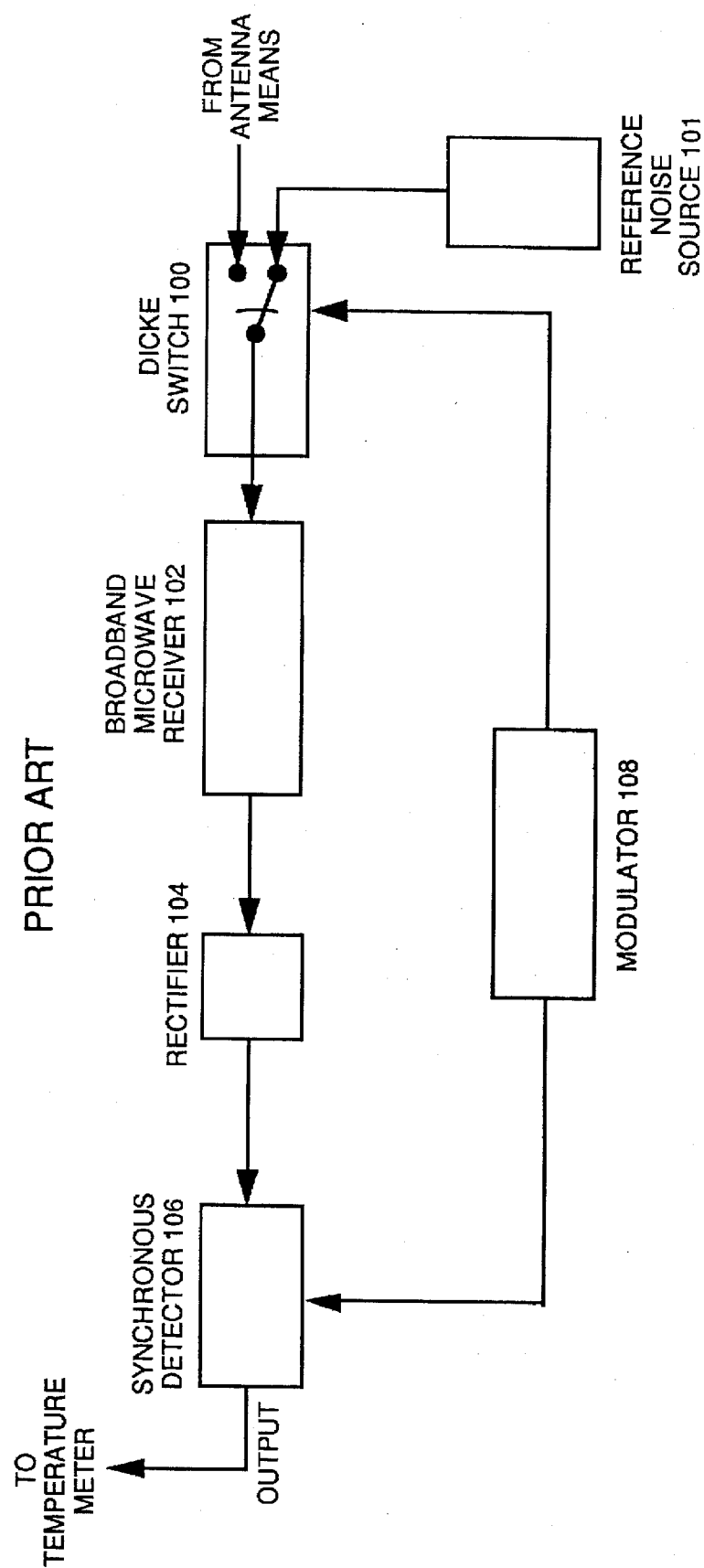
FIGS. 1a and 1b illustrate different prior-art species of microwave radiometers used to measure the temperature of a specimen.

FIG. 1a illustrates a relatively simple prior-art implementation of a microwave radiometer. The output from calibrated reference noise source 101 is applied to a first input of so-called Dicke switch 100 and the output from the antenna means is applied to a second input thereof. The output of Dicke switch 100 is applied to the input of broadband microwave receiver 102 and the output of receiver 102, after rectification by rectifier 104, is applied as an input to synchronous detector 106. The output of Dicke switch 100, under the control of modulator 108, is cyclically oscillated back and forth between its first and second inputs at a given rate. At the same time, synchronous detector 106 is cyclically operated under the control of modulator 108 at the same given rate. The result is the output amplitude from synchronous detector 106 during each cycle varies from a first level indicative of the intensity of the microwave noise received by the antenna means and the intensity of the microwave noise generated by reference noise source 101. The specimen temperature is indicated by a properly calibrated temperature meter responsive to the difference between the first and second levels.

Figure 1B:
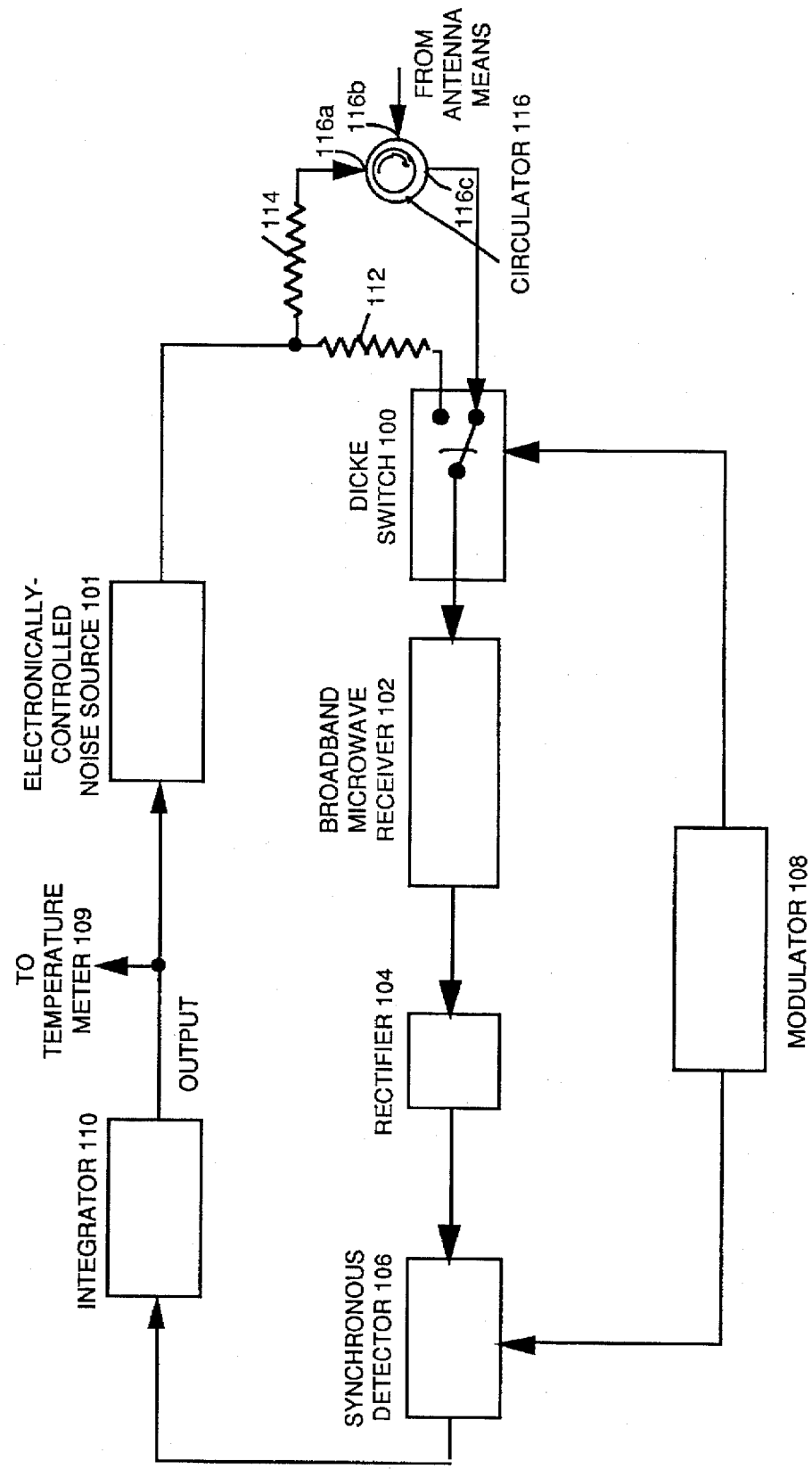

FIG. 1b illustrates a somewhat more sophisticated prior-art implementation of a microwave radiometer. As shown in FIG. 1b, the output from synchronous detector 106, after being integrated by integrator 110, constitutes the output to the temperature meter. Further, the output to the temperature meter from integrator 110 is fed back as a control input to an electronically-controlled reference noise source 101 (i.e., the intensity of noise generated by electronically-controlled noise source 101 varies directly with the level of the output to temperature meter 109). The output from electronically-controlled noise source 101 is applied through power-splitting resistance 112 to a first input of Dicke switch 100 and is applied through power-splitting resistance 114 to first port 116a of circulator 116. The microwave antenna means is coupled to second port 116b of circulator 116 and microwave radiation arriving at third port 116c of circulator 116 is applied to a second input of Dicke switch 100. As indicated by the circulator 116 arrow in FIG. 1b, microwave radiation travels clockwise from first port 116a to second port 116b of circulator 116, and from second port 116b to third port 116c of circulator 116. Unless the impedance match, as seen from second port 116b of circulator 116, happens to be perfect, some of the noise microwave radiation arriving at second port 116b of circulator 216 will travel back through the microwave antenna means to the specimen, thereby substantially compensating for the impedance mismatch. Further, the feedback of the integrated output to temperature meter 109 as a control input to electronically-controlled noise source 101 results in the intensity of the noise microwave radiation applied to the first input of Dicke switch 100 being automatically adjusted to the point that it is substantially equal to and balances the intensity of the microwave radiation applied from the third port of circulator 116 to the second input of Dicke switch 100.

The aforesaid U.S. Pat. No. 5,149,198 also discloses a Dicke switch replacement which employs two hybrid circuits, preferably in the form of hybrid rings, to permit amplification of both unknown and reference noise signals in a manner which, besides increasing the signal-to-noise ratio of the radiometer, is immune to differences in amplifier characteristics for each of the two signals and permits the sensitivity of the radiometer to be doubled.

Figure 2:
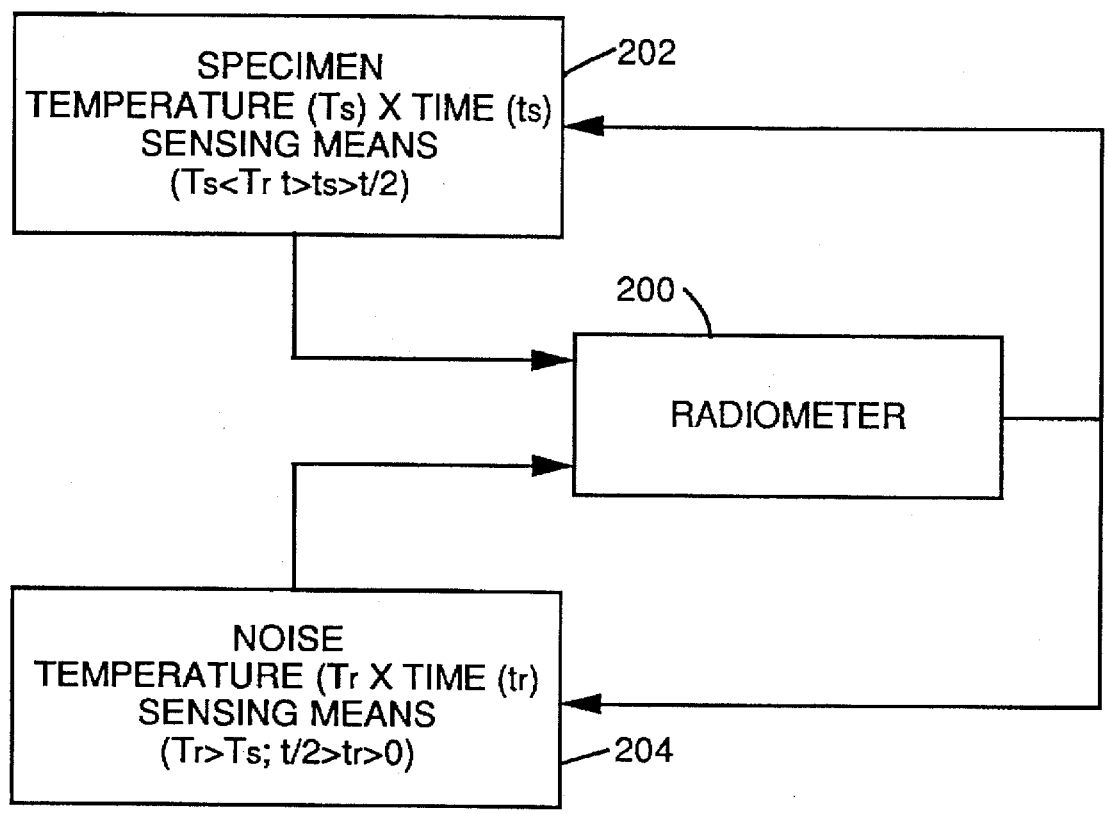
FIG. 2 is functional block diagram illustrating the principles of a first improvement in the operation of microwave radiometers, wherein the microwave noise from a specimen, which has a temperature significantly below that of a reference noise source, is applied as an input to the radiometer for a longer time than is the reference noise source.

In the prior-art implementations of a microwave radiometer, a Dicke switch or its replacement is operated with a 50% duty cycle for respectively controlling the application of each of the specimen signal and the reference noise signal as inputs to the radiometer. In accordance with a first improvement of the present invention, a relatively low absolute temperature specimen signal (such as the body tissue of a patient) is applied as an input to the radiometer with a duty cycle of more than 50% (preferably close to 100%), while a reference noise signal (e.g., obtained from a heated termination or a diode or gas tube reference noise source) indicative of a temperature higher than that of the specimen is applied as an input to the radiometer with a duty cycle of less than 50%. More specifically, as functionally shown in the FIG. 2 block diagram, means 202 applies the relatively low absolute temperature $T_s$ specimen signal as a first input to radiometer 200 for a time $t_s$ which is more than 50% of a cycle period time t and means 204 applies the relatively high absolute temperature $T_r$ reference noise signal as a second input to radiometer 200 for a time $t_r$ which is less than 50% of the cycle period time t. By feeding back an output from radiometer 200 as a duty-cycle adjusting, null-seeking input to means 202 and means 204, the duty cycle can be adjusted to the point at which:

$$T_s \times t_s = T_r \times t_r; \text{ so that } T_s = T_r \times (t_r/t_s). \tag{1}$$

Thus, by knowing the temperature of the reference noise signal (which can be accurately measured by conventional instruments) and the duty-cycle, the temperature of a specimen can be calculated and displayed using appropriate corrections if necessary. For example, if the absolute reference noise temperature $T_r$ is 10% greater than the absolute temperature $T_s$ of a body tissue specimen, the respective integrated microwave thermal noise energies $T_s = T_s \times t_s$ and $T_r = T_r \times t_r$ (i.e., power×time) of each will be made equal by adjusting the duty-cycle to look at the body tissue for 11-ms and the reference noise source for 10-ms.

Another advantage of using a hotter than ambient reference noise source and a duty-cycle favoring the specimen is that the sensitivity increases since the noise from the specimen is integrated for more than the one-half the time of the conventional 50% duty cycle. This is applicable to heated terminations when used as the reference noise source and even more so to diode or gas tube noise sources where the effective noise temperatures are very much greater than the ambient body tissue specimen temperature (e.g. 15-db greater). In this case, the switch will be looking at the body tissue for a large majority of the time.

While a conventional Dicke-switch circuit at the input of the radiometer may be employed to implement the present invention, it is not to be preferred because most electronic switches have significant insertion loss increasing the noise figure of the radiometer and reducing sensitivity. This problem is overcome by employing the implementation shown in FIG. 3 which moves the switching function well away from the input.

Figure 3:
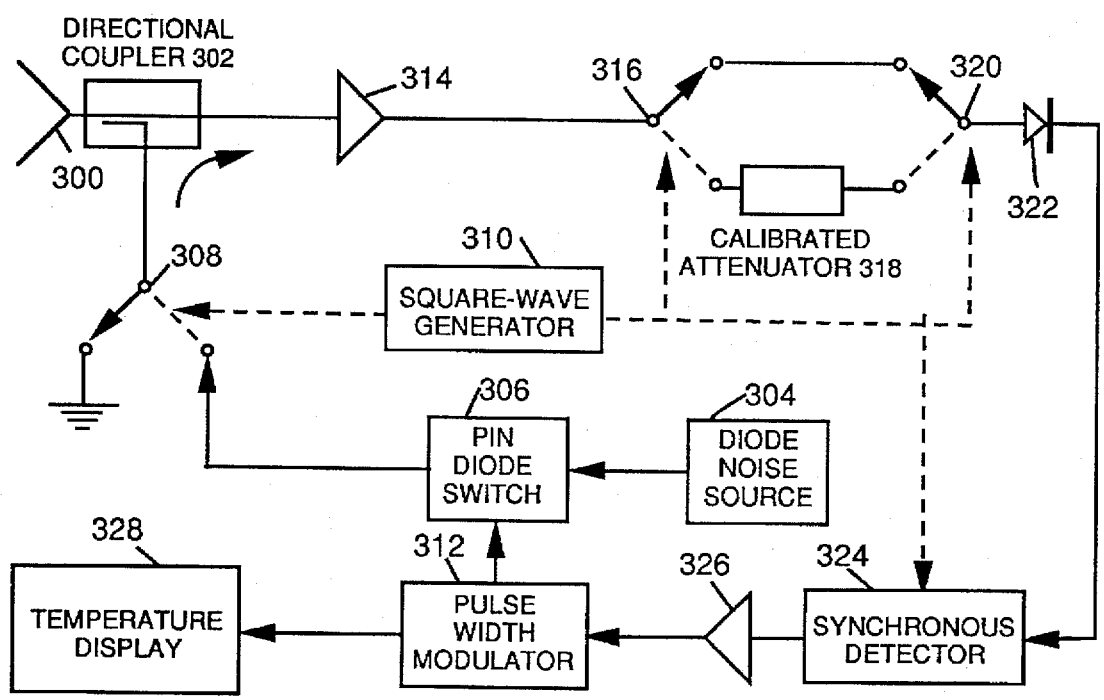
FIG. 3 diagrammatically illustrates a preferred structure for implementing the first improvement of FIG. 2, and FIGS. 3a, 3b, 3c and 3d illustrate different modifications of the structure of FIG. 3.

Referring to FIG. 3, there is shown antenna 300, directional coupler 302, diode noise source 304, PIN diode switch 306, SPDT switch 308, square-wave generator 310, pulse width modulator 312, high-gain, low-loss microwave amplifier 314, SPDT switch 316, calibrated attenuator 318, SPDT switch 320, microwave detector 322, synchronous detector 324, feedback amplifier 326 and temperature display 328.

Under the control of square-wave generator 310, SPDT switches 308, 316 and 320 occupy each of their first switch positions (indicted by solid lines) and their second switch positions (indicted by dashed lines) for 50% of each square-wave cycle, while detector 324 is synchronously operated with the operation of these switches. During the entire 50% of each square-wave cycle in which switch 308 is in its first switch position, the coupler element of directional coupler 302 is grounded preferably through a matched load (not shown), rather than leaving switch 308 open in its first switch position. Therefore, only microwave noise energy received by antenna 300 (indicative of the absolute temperature $T_s$ of a specimen, such as a patient's body tissue) is forwarded through directional coupler 302, amplifier 314 and switches 316 and 320 in their first switch positions as the input to detector 322. The output from detector 322 is then forwarded as the error signal input to synchronous detector 324. However, during the entire 50% of each square-wave cycle in which switch 308 is in its second switch position, directional coupler 302 sums the specimen microwave noise energy from antenna 300 with the microwave noise energy forwarded thereto from diode noise source 304 through PIN diode switch 306. This summation microwave energy is then forwarded through amplifier 314, switch 316 in its second switch position, attenuator 318 and switch 320 in its second switch position as the error signal input to detector 322. The output from detector 322 is then forwarded as the input to synchronous detector 324. The output from synchronous detector 324, after being amplified by feedback amplifier 326, is applied as an input to modulator 312 to control the width of the output pulses generated thereby. These output pulses from pulse width modulator 312 are then applied as an input to PIN diode switch 306 to limit in response thereto the proportion of the time of the 50% of each square-wave cycle in which switch 308 is in its second switch position during which noise energy from diode noise source 304 is combined with the specimen noise energy in directional coupler 302.

Calibrated attenuator 318 has a of known value A. During the 50% duty cycle when attenuator 318 is switched in, the amount of reference noise is automatically adjusted for a zero detector output $V_d$ by a null-seeking feedback circuit within pulse width modulator 312. Zero-balance occurs only when the attenuated combined specimen and reference noise energy equals the unattenuated reference noise energy. Therefore, $$V_d=0 \text{ when } T_s=A[T_s+T_r]; \text{ thus, } T_s=T_r[A/(1-A)]. \quad (2)$$

Preferably, calibrated attenuator 318 is a 3 db attenuator so that the value of A=0.5, which results in $T_s=T_r$.

In FIG. 3, the time $t_s$ is unity and the duty cycle of pulse width modulator 312 is proportional to the amount of reference noise energy $T_r=T_r \times t_r$ needed to balance the circuit. Therefore, employing equation 1 set forth above, the average DC voltage of the variable duty cycle pulse derived by modulator 312 provides a linear voltage output for temperature display 328 of the temperature $T_s$. The DC output can be used as a relative value in a temperature comparison mode of operation without calibration. To provide a temperature readout, the output must be calibrated against a standard. With calibration, a relatively linear output calibrated in the Celsius scale can be obtained. If switch 308 in its first switch position is not terminated in a matched load, it is likely to contribute noise (because an electronic switch "open" is not a complete open) that results in introducing error in the temperature reading of display 328. A matched load termination prevents such error.

One advantage of the "noise-added" approach of the FIG. 3 embodiment is that it provides a means of doubling the collected specimen noise energy compared to that collected by a conventional Dicke switch by continuously receiving the energy from the source and introducing the reference comparison switching at the end of the microwave circuit, rather than by switching back and forth a Dicke switch at the start of the microwave circuit. Further, at the end of the microwave circuit, the microwave signals are at their maximum value, thereby minimizing switch feed-through effects which are synchronous with the detection circuit.

Figure 3A:
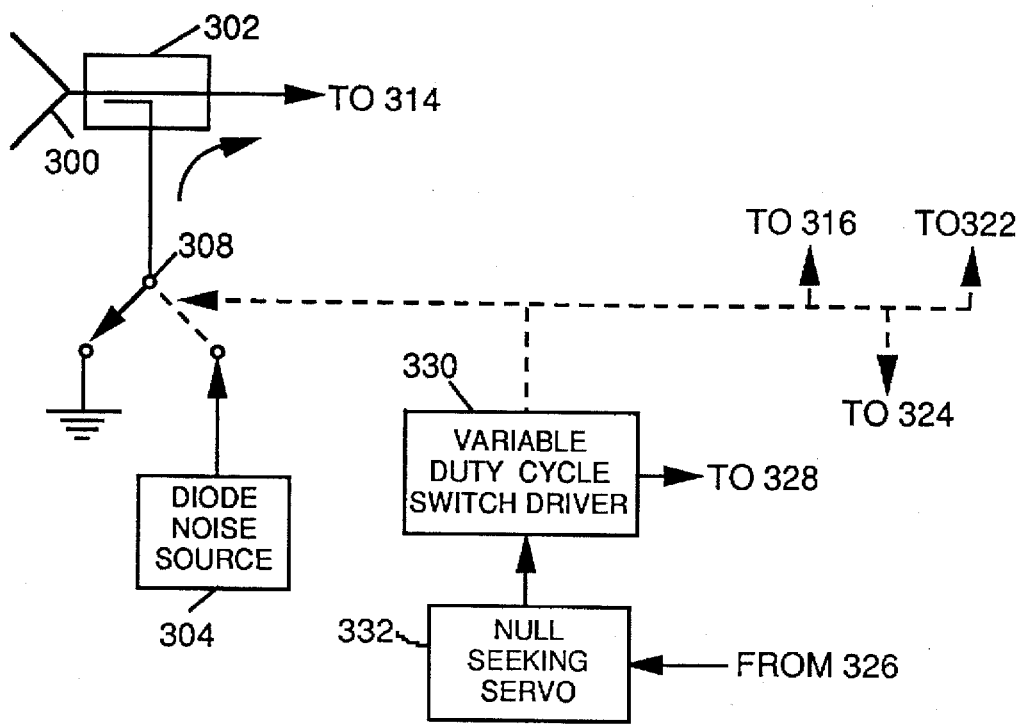

The structure shown in FIG. 3 uses pulse width modulator 312 and PIN diode switch 306, in cooperation with switch 308 being operated at a 50% duty cycle by square-wave generator 310, to control the time $t_r$ as the variable employed in solving above equation 1. However, the variable time $t_r$ may be alternatively controlled by replacing such structure of FIG. 3 with that shown in FIG. 3a. In FIG. 3a, diode noise source 304 is applied directly to switch 308 and the duty cycle of each of switches 308, 316 and 320 and synchronous detector 324 is determined by the output from variable duty cycle switch driver 330. The duty cycle of switch driver 330 is varied by null seeking servo 332 in response to the output from feedback amplifier 326 applied as an input to servo 332. This results in switches 308, 316 and 320 being in their second switch position for time $t_r$ of each cycle of switch driver 330, rather than for 50% of each cycle. An average DC voltage proportional to the the variable duty cycle derived by switch driver 330 provides a linear voltage output for temperature display 328.

The variable parameter in above equation 1 may be $T_r$, rather than $t_r$. This is the case in the modification of FIG. 3 broadly shown in FIG. 3b, in which variable noise source 334 derives a noise-power output corresponding to temperature $T_r$ in response to the output from feedback amplifier 326. This noise-power output is forwarded to directional coupler 302 during the 50% of each cycle of square-wave generator 310 in which switch 308 is in its second switch position. Further, variable noise source 334 derives a temperature-indicating output that is forwarded to temperature display 328.

Figure 3B:
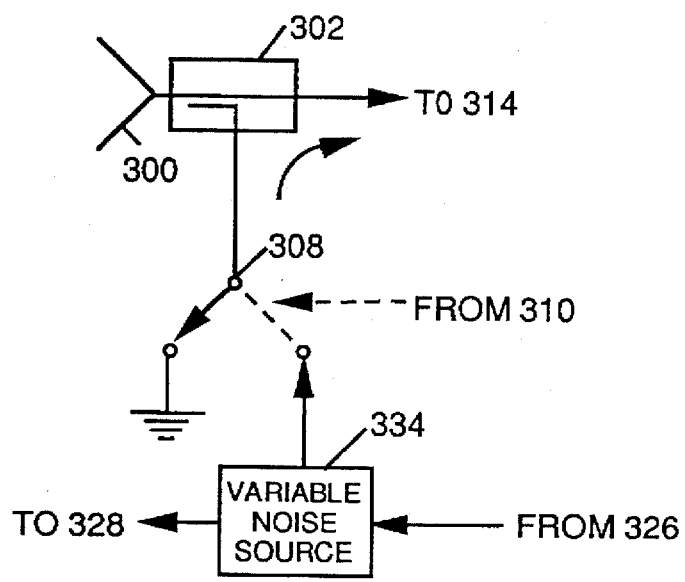
Figure 3C:
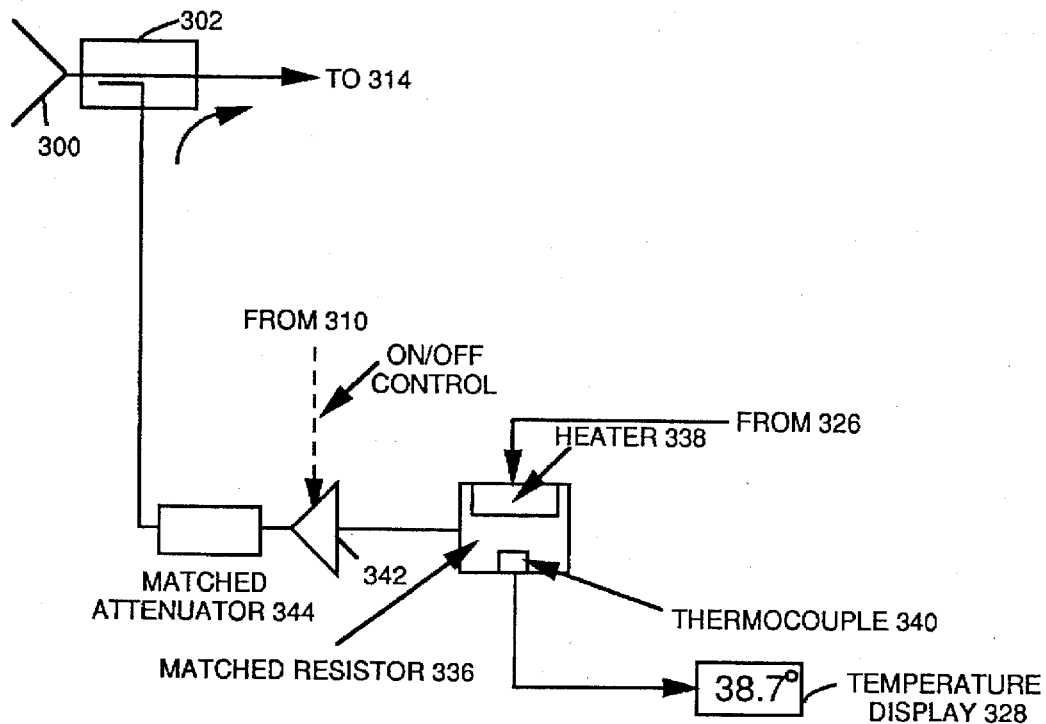

FIG. 3c shows one specific example of the modification shown in FIG. 3b employing a unit comprising matched resistor 336 variably heated by heater 338 in response to the output from feedback amplifier 326 to a temperature $T_r$ that is measured with thermocouple 340. Amplifier switch 342, which is responsive to a 50% duty cycle on/off control from square-wave generator 310 and which replaces switch 308, forwards the matched-resistor output to directional coupler 302 through matched attenuator 344.

Heater 338 is used to set the temperature of matched resistor 336 which acts as a termination equivalent to a black body radiator in that it generates microwave energy as a function of its temperature, as is known art setting the temperature of the heated resistor so as to balance the input unknown using the feedback circuit. This balance is obtained when the temperature-produced power from the resistor is amplified sufficiently to overcome the coupling loss of the directional coupler 302 so that the attenuated and unattenuated paths are equalized at the output of detector 322 (shown in FIG. 3). This arrangement is especially useful when the overall gain between the output from heated matched resistor 336 and the output of detector 322 is unity (i.e., the gain of amplifiers 342 and 314 exactly balances the loss from matched attenuator 344 and directional coupler 302). This results the temperature of heated matched resistor 336 being the same as the specimen (e.g., body tissue) temperature. This permits thermocouple 340 (or, alternatively, a thermistor, resistor temperature detector, or thermometer type temperature measuring instrument) to be used to directly measure and display the temperature of heated matched resistor 336. The result is that when the circuit is in balance, the temperature of heated matched resistor 336 becomes the same as the specimen temperature without the need for correction or other calibration.

The above-described approach used to directly measure and display the temperature of a heated matched resistor is not, per se, novel. In this regard, reference is made to the aforesaid U.S. Pat. No. 5,149,198. Therefore, this approach is not restricted to a modification of the FIG. 3 radiometer structure, but can be used in any conventional or unconventional Dicke-switch radiometer or any other type of radiometer that uses a noise source as a reference.

Figure 3D:
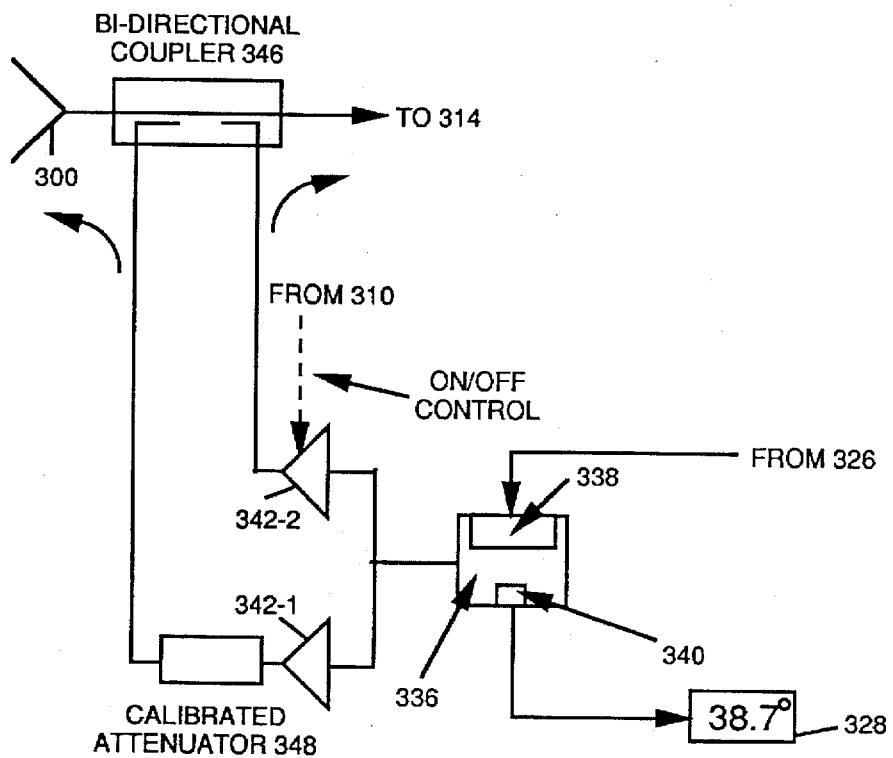

FIG. 3d shows a modification of the FIG. 3c structure which provides a correction for the effective emissivity of the specimen (e.g., body tissue). In the balanced state, heated matched resistor 336 is at the same temperature as the specimen except for the possible error produced by a non-perfect emissivity. That condition is caused by an imperfect match between antenna 300 and the specimen to which it is coupled. In FIG. 3d, this non-perfect emissivity problem is solved by replacing directional coupler 302 in FIG. 3c with bi-directional coupler 346 in FIG. 3d. that includes two coupling elements. The output of heated matched resistor 336 is applied through amplifier 342-1 and calibrated attenuator 348 to a first of the two coupling elements of bi-directional coupler 346 for coupling microwave power back through antenna 300 toward the specimen, and is also applied through amplifier 342-2 (which has an on/off control from square-wave generator 310 applied thereto and which is equal in gain to amplifier 342-1) to a second of the two coupling elements of bi-directional coupler 346 for coupling microwave power forward to amplifier 314. Calibrated attenuator 348 attenuates power by the same amount as calibrated attenuator 318 of FIG. 3 for proper balance during the switching cycle. Proper balance could also be done by offsetting the gain of amplifier 342-1 with respect to that of amplifier 342-2 without the need for calibrated attenuator 348, but is more accurately achieved by using equal gain amplifiers 342-1 and 343-2 and employing calibrated attenuator 348.

It is apparent from the aforesaid Lüdeke and Köhler article that closed-loop radiometric circuitry (including those employed in FIGS. 2b and 3d) which correct for the effective emissivity of a specimen (e.g., body tissue) tend to introduce instability unless the time constants of the circuitry are precisely matched (i.e., the application of the correction, changes the temperature reading, which changes the correction, etc., causing the temperature reading to hunt or oscillate). In practice, insuring that the time constants are and remain precisely matched increases the required complexity of the radiometric closed-loop circuitry.

However, in accordance with a feature of the present invention, this instability problem is overcome by replacing closed-loop emissivity-correction circuitry with open-loop emissivity-correction circuitry that is completely separated from the reference noise source of the radiometer. Further, such open-loop emissivity-correction circuitry provides fast read out caused by antenna-to-body contact changes because the emissivity-correction circuitry is not part of the slow loop of the radiometer/integrator measurement circuit. In this regard, reference is made to the open-loop emissivity-correction circuitry shown, respectively, in FIGS. 4a, 4b and 4c.

Figure 4A:
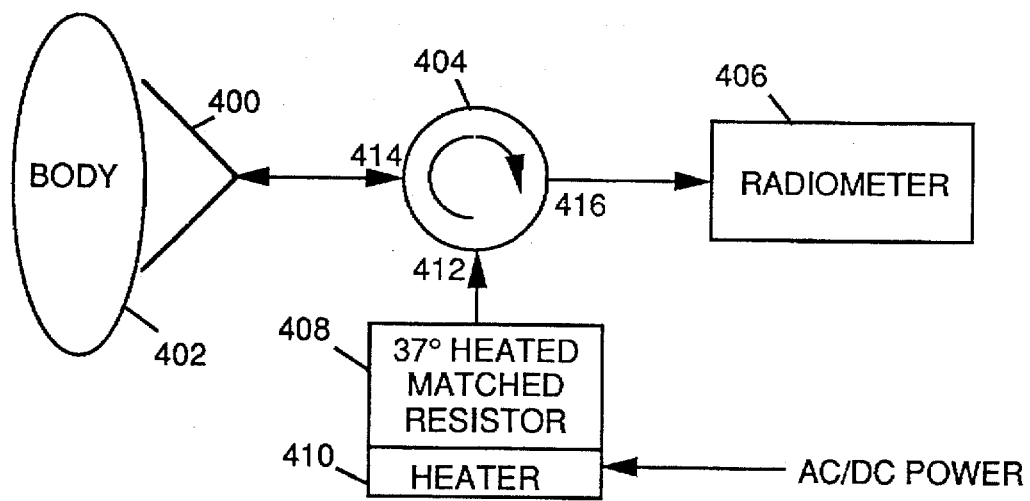
FIGS. 4a, 4b and 4c different species of open-loop means for reducing emissivity-error in the measurement with a radiometer of the temperature of the body tissue of a patient, which constitute a second improvement in the operation of microwave radiometers.

FIG. 4a shows a very simple open-loop emissivity-correction circuitry for a radiometer that substantially reduces emissivity-based error in the measurement of body temperature. FIG. 4a shows antenna 400, body 402 of a person, circulator 404, radiometer 406 and matched resistor 408 which is thermostatically heated to a temperature of 37° C. by heater 410 which is energized by AC/DC power applied to heater 410. 37° C. heated matched resistor 408 is coupled to first input port 412 of circulator 404 (which circulates microwave power in a clockwise direction), antenna 400 is coupled to second input port 414 of circulator 404 and output port 416 of circulator 404 is coupled as the signal input to radiometer 406.

As known, the amount of emissivity error depends on the percentage of mismatch reflectivity at the body-antenna interface and the effective temperature difference ΔT between the body temperature and the effective temperature of the microwave noise power emitted back from antenna 400 to body 402 at the interface. Should antenna 400 be coupled directly to the input of radiometer 406 without circulator 404 being present, room temperature (about 22° C.) is the effective temperature of this microwave noise. However, in FIG. 4a, the effective temperature of this microwave noise power becomes the 37° C. of heated matched resistor 408, rather than the 22° C. room temperature. Assume, by way of example, that the mismatch reflectivity is 30% and the person's body temperature is 41° C. (i.e., high fever). In this case, the FIG. 4a structure reduces the emissivity error to 0.3(41−37)=1.2 C. from the 0.3 (41−22)=5.7 C. emissivity error which would occur in the absence of the FIG. 4a structure.

Figure 4B:
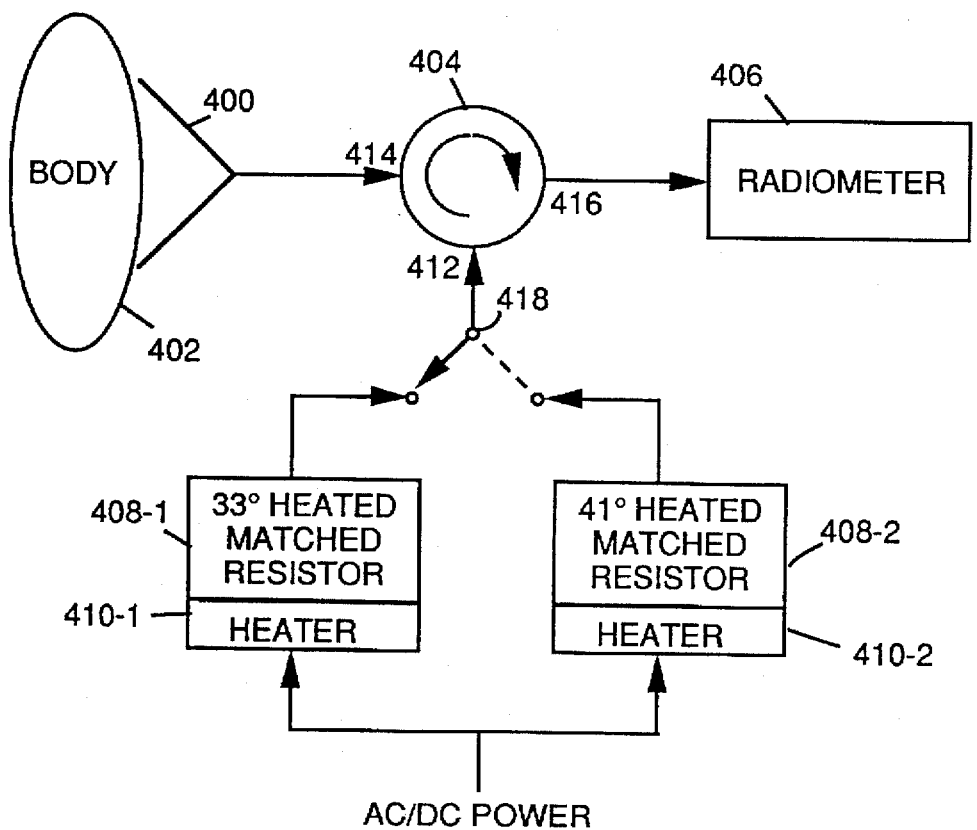

FIG. 4b shows a modification of the FIG. 4a structure in which a pair of matched resistors 408-1 and 408-2 that are respectively heated by heaters 410-1 and 410-2 are substituted for single matched resistor 408 and heater 410 of FIG. 4a. Matched resistor 408-1 is thermostatically heated to a lowest expected body temperature (assumed to be 33° C.) and matched resistor 408-2 is thermostatically heated to a highest expected body temperature (assumed to be 41° C.) which average to the 37° C. temperature of matched resistor 408 of FIG. 4a. In FIG. 4b, SPDT switch 418, which is toggled back and forth at a high frequency rate compared to the frequency rate of the synchronous detector of radiometer 406, alternately applies the microwave noise power from heated matched resistors 408-1 and 408-2 as an input to port 412 of circulator 404.

Figure 4C:
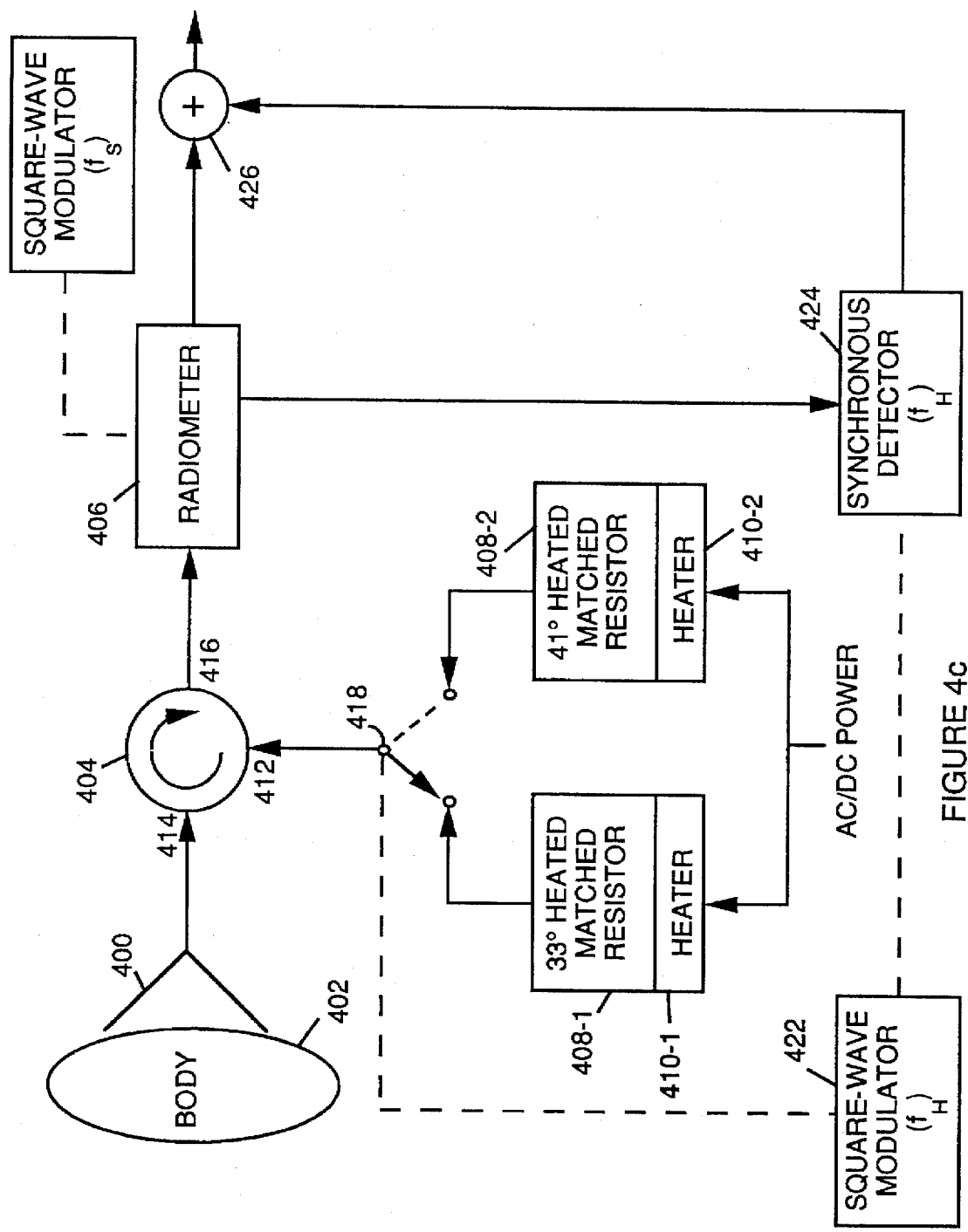

The respective abilities of the FIG. 4b structure, without further modification, and the FIG. 4a structure described above to reduce emissivity error are substantially equal to one another. However, in order to further reduce emissivity error, the structure of FIG. 4b is preferably incorporated as a component of the structure shown in FIG. 4c. FIG. 4c shows square-wave modulator 420 of radiometer 406 (which operates the synchronous detector of radiometer 406 at a relatively low frequency rate $f_L$) extracted from radiometer 406 and also shows square-wave modulator 422, which operates at a relatively high frequency rate $f_h$, that is used to toggle SPDT switch 418 back and forth. Further, auxiliary synchronous detector 424, which has applied as an input thereto the same input applied to the synchronous detector of radiometer 406, is operated at the relatively high frequency rate $f_h$ of square-wave modulator 422. The DC output of auxiliary synchronous detector 424 constitutes an emissivity-error correction component which is algebraically added to the DC output of the synchronous detector of radiometer 406 in summer 426 to provide an open-loop, emissivity-corrected radiometer output from FIG. 4c.

Figure 5:
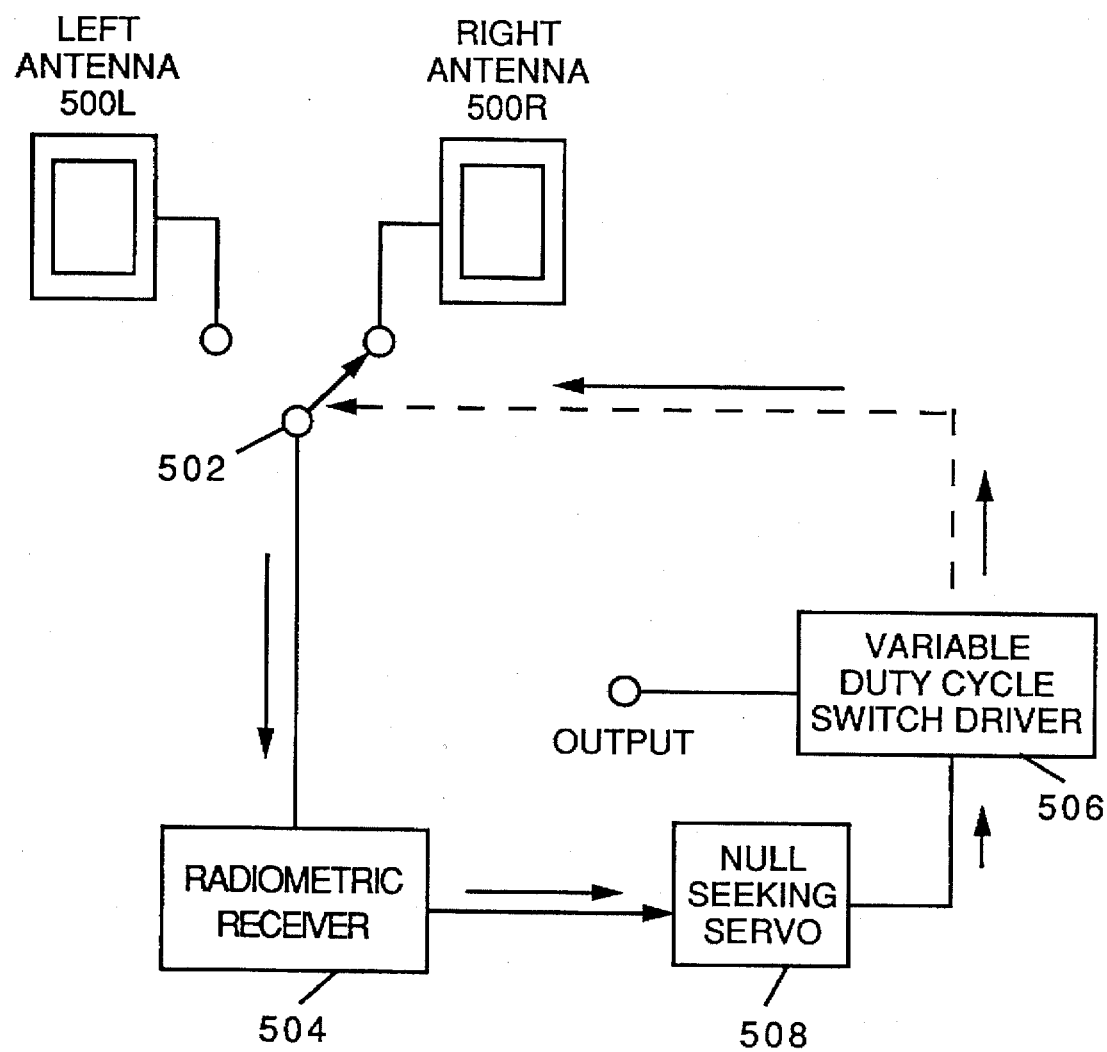
FIG. 5 illustrates a radiometer embodiment for measuring differential temperature between two specimen source.
Figure 5A:
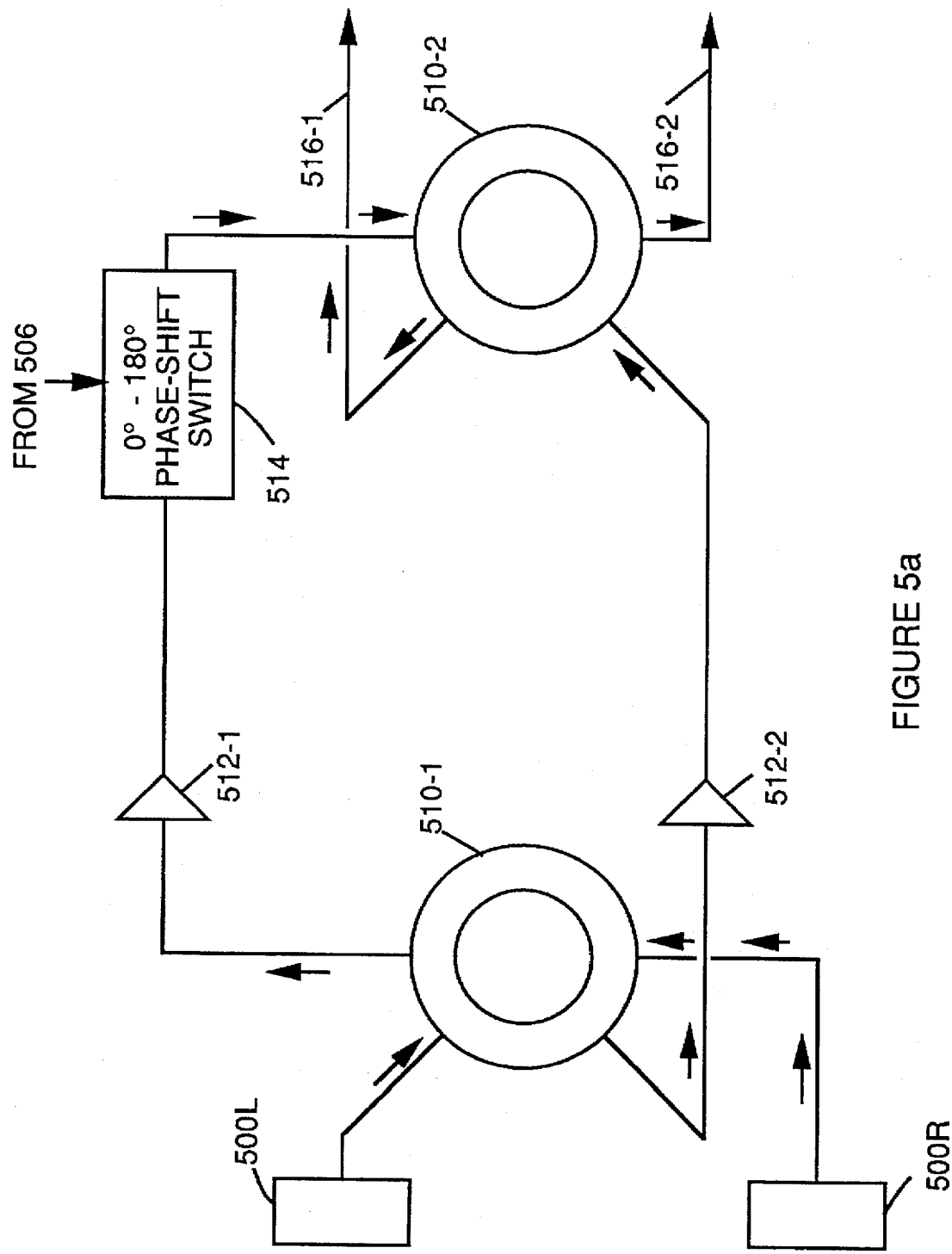
FIG. 5a illustrates a modification of the FIG. 5 embodiment, which FIGS. 5 and 5a embodiments constitute a third improvement in the operation of microwave radiometers.

As shown in FIG. 5a, structure similar to that shown in FIG. 3a may be used with a Dicke-switch differential microwave radiometer to compare the temperature $T_L$ of a first specimen emitting microwave noise power received by left antenna 500L with the temperature $T_R$ of a second specimen emitting microwave noise power received by right antenna 500R. Specifically, Dicke switch 502 alternately connects antenna 500L or antenna 500R as an input to radiometric receiver 504. Dicke switch 502 is driven by a variable duty cycle switch driver 506, which, in turn, is part of a feedback loop in which null seeking servo 508 adjusts the duty cycle of driver 506 in accordance with the output from receiver 504 until the integrated noise energy $T_L$ forwarded as an input to receiver 504 during the time Dicke switch 502 connects antenna 500L thereto equals the integrated noise energy $T_R$ forwarded as an input to receiver 504 during the time Dicke switch 502 connects antenna 500R thereto. The radiometric temperature difference between antennas 500L and 500R is determined at the output from driver 506 from a measurement of the driver's duty cycle. A disadvantage of this design is that the signals must pass through a lossy Dicke switch before amplification in receiver 504. This degrades the signal-to-noise ratio and consequently degrades the measurement accuracy as well.

Separate amplifiers cannot be placed after each antenna and before the Dicke switch, as very high errors will result due to the gain mismatch between the amplifiers.

This problem is overcome by the use of the type of hybrid ring structure shown in FIG. 5a (which is similar to that disclosed in the aforesaid U.S. Pat No. 5,149,198). As shown in FIG. 5a, the two signals from antennas 500L and 500R pass through first hybrid ring 510-1, one output of which is the sum of the two antenna signals, and the other output of which is the difference of the two antenna signals. One of these sum and difference signals is amplified to a suitable power level by high-gain, low-loss amplifier 512-1 and the other of these sum and difference signals is amplified to a suitable power level by high-gain, low-loss amplifier 512-2. One of the two amplified signals then passes through a 0°–180° phase shift switch 514, whose duty cycle can be electronically controlled by switch driver 506. This amplified, switched signal and the other amplified, unswitched signal are both fed to second ring hybrid 510-2. Each of the two outputs (sum and difference) of second ring hybrid 510-2 alternately switches between the antenna 500-L signal and the antenna 500-2 signal in accordance with the position of the 0°–180° phase shift switch 514. Either output 516-1 and 516-2 from second ring hybrid 510-2 can be used in the same manner as the Dicke switch output of the structure shown in FIG. 5 to control the switch duty cycle in a closed feedback loop corresponding to that shown in FIG. 5. Due to the symmetry of the architecture and to the fact that both antenna signals always pass through both amplifiers 512-1 and 512-2, the mismatch between the two amplifiers does not contribute significantly to measurement errors.

Figure 5B:
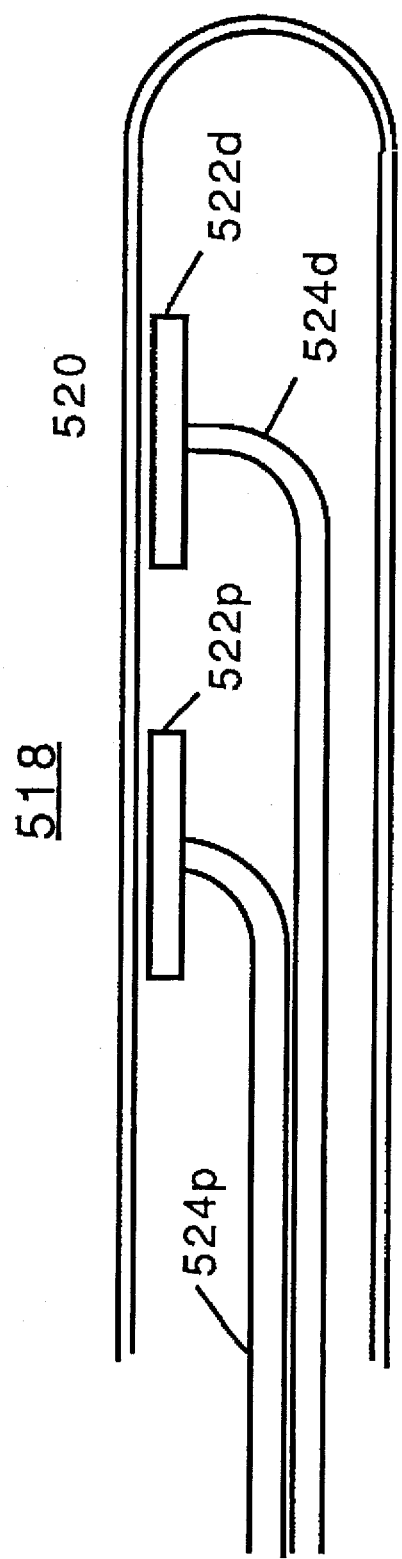
FIGS. 5b and 5c, respectively, illustrate the structure of a differential-temperature applicator for the FIG. 5 or 5a radiometer, and the use of such an applicator in the diagnosis of prostate cancer.

FIG. 5b shows the structure of differential microwave radiometer applicator 518 suitable for use in medical diagnostics in making differential subsurface body tissue temperature measurements when inserted into natural openings of the body. Specifically, applicator 518 comprises catheter 520 having a closed front end and an open rear end. Within catheter 520 are situated closely spaced antennas 522p and 522d, with antenna 522p being located proximate to the open rear end of catheter 520 and antenna 522d being located distal to the open rear end and nearer to the closed end of catheter 520. Antennas 522p and 522d are connected to a differential radiometer (not shown) situated outside of applicator 518 by coaxial cables 524p and 524d which exit through the open rear end of catheter.

Figure 5C:
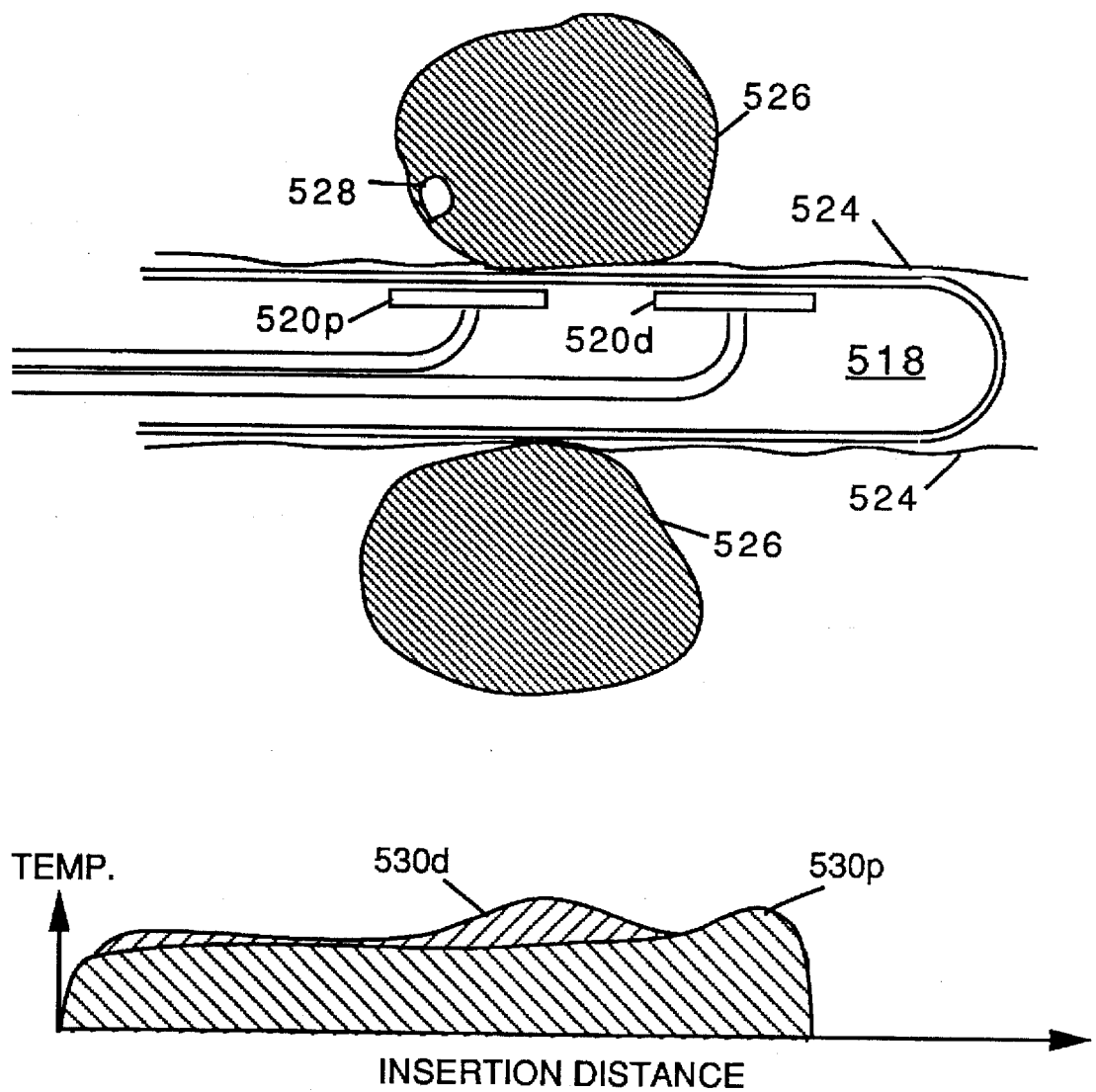

It is known that the temperature of cancerous body tissue is higher than that of normal body tissue. FIG. 5c considers the case, by way of example, in which differential microwave radiometer applicator 518 is slowly inserted along the length of a patient's urethra 524 so that it passes by prostate 526 which includes a cancerous lesion 528 is employed in the diagnosis of prostate cancer. Further, FIG. 5c shows respective graphs 530p and 530d of (1) the temperature of proximate antenna 520p as a function of its insertion distance in urethra 524 and (2) the temperature of distal antenna 520d as a function of its insertion distance in urethra 524. As applicator 518 is inserted, distal antenna 520d passes cancerous lesion 526 at a smaller insertion distance than does proximate antenna 520p. Thus, the temperature indicated by graph 530d is significantly higher than the temperature indicated by graph 530p when distal antenna 520d passes lesion 528, and is significantly lower when proximate antenna 520p passes lesion 528. Thus, the determination of differential temperature as a function of insertion distance not only indicates the presence of cancerous prostate lesion 528, but also its location.

Mammograph equipment is known in the art for taking an X-ray images of a patient's breast for use by a radiologist in identifying and locating a cancerous lesion in the breast, should it be present. It would be desirable to also make use of the known fact that the temperature of cancerous body tissue is higher than that of normal body tissue to supplement this identification and location of a cancerous lesion in the breast. In this regard, reference is made to FIGS. 6, which, in functional form, shows a cooperative combination of conventional mammograph equipment 600 with novel radiometric equipment, that comprises upper and lower antenna stages 602U and 602L (shown in more detail in FIG. 6a) coupled by cables 604U and 604L to scanning radiometer and temperature reading equipment 606.

Conventional mammograph equipment 600 comprises X-ray adjustment 608 for adjusting the position of X-ray tube 610, adjustment 612 for adjusting the position of positioning guide 614 and adjustment 616 for adjusting the position of X-ray film holder 618. In operation, a patient's breast is placed between positioning guide 614 and film holder 618, which are adjusted by technicians to lightly compress the breast therebetween in a manner that minimizes the chance of metastasis of any cancerous lesion which may be present taking place.

Figure 6:
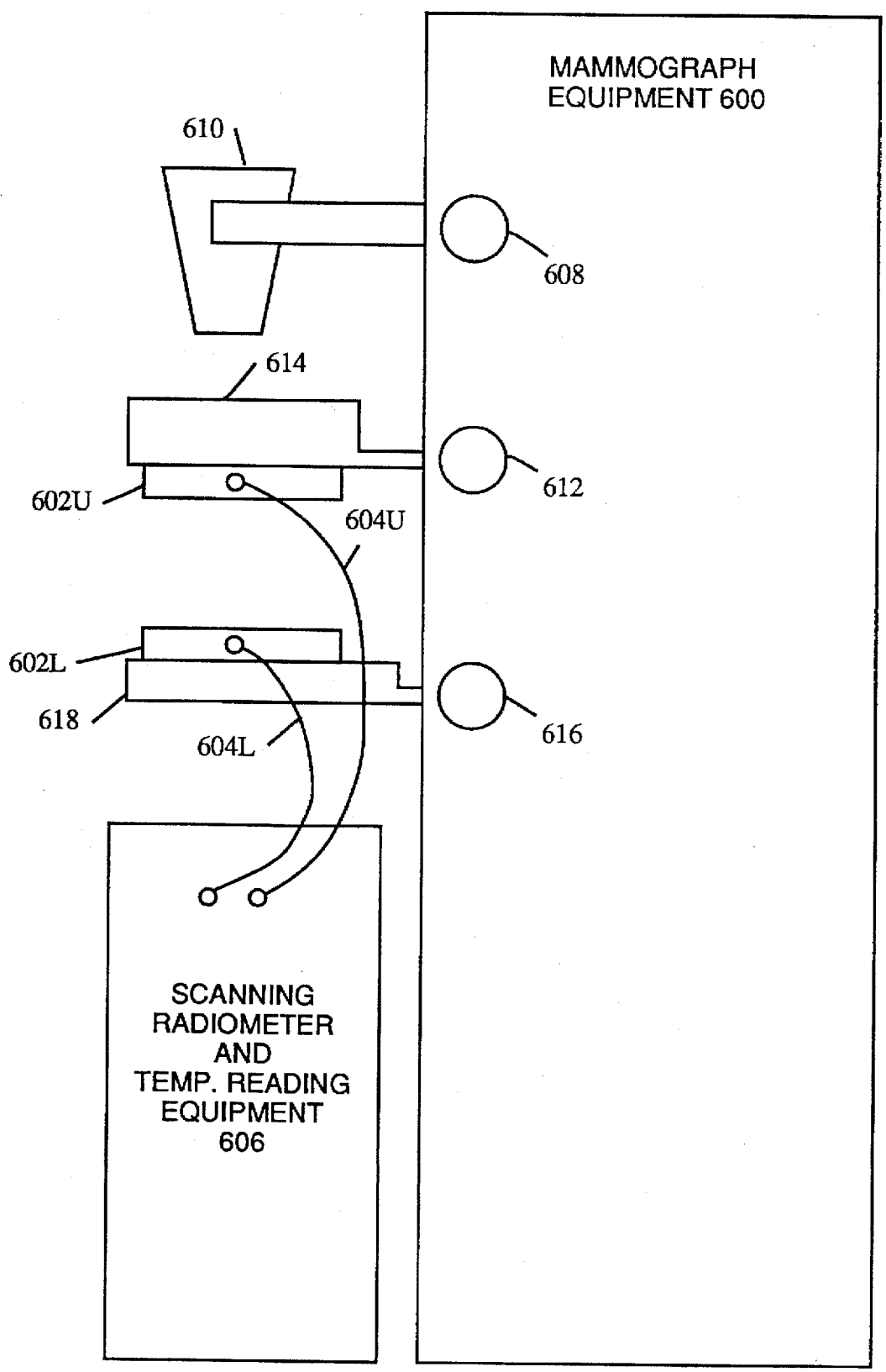
FIGS. 6 and 6a illustrate a combination of radiometric equipment with mammograph equipment for improved detection of a cancerous lesion within the breast, which constitute a fourth improvement in the operation of microwave radiometers.
Figure 6A:
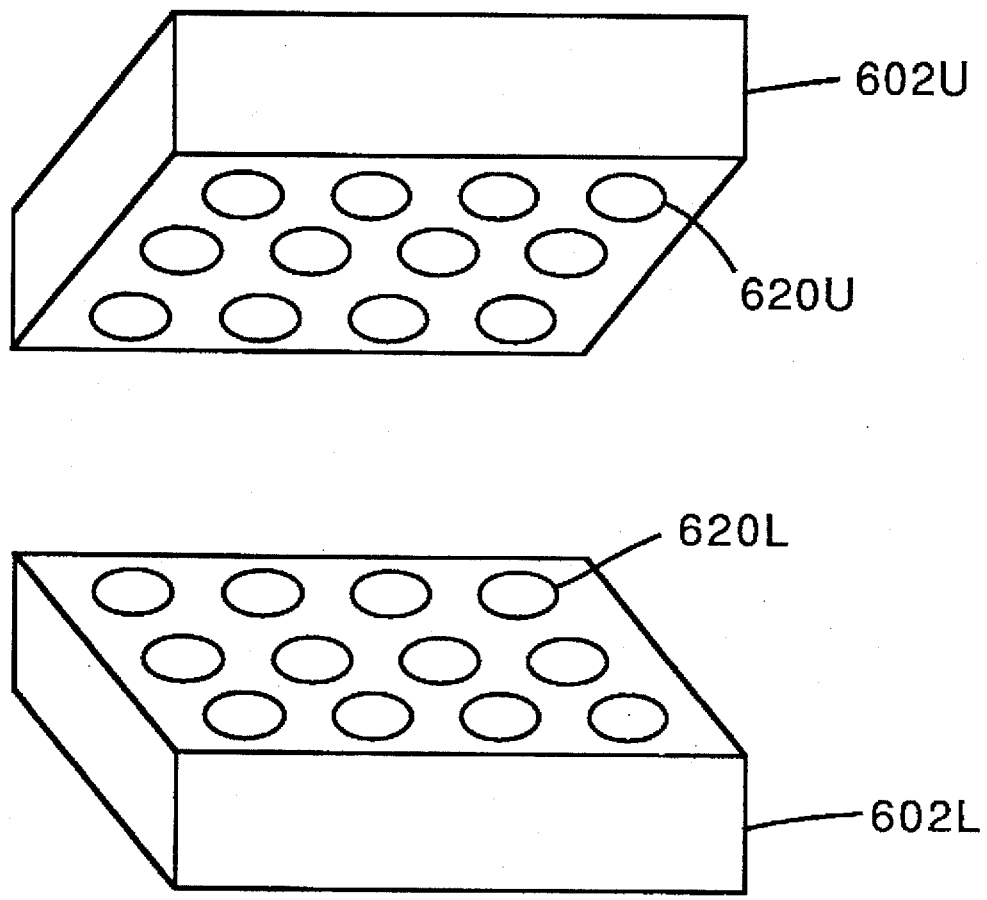

As shown in FIG. 6, upper antenna stage 602U is attached to the bottom of positioning guide 614 and lower antenna stage 602L is attached to the top of film holder 618, so that, with such attachments, the patient's breast is lightly compressed between upper antenna stage 602U and lower antenna stage 602L. As shown in FIG. 6a, a 2-dimensional upper array of radiometer antennas 620U are attached to the bottom surface of upper antenna stage 602U, and a corresponding 2-dimensional lower array of radiometer antennas 620L are attached to the top surface of lower antenna stage 602L. Thus, while the patient's breast is lightly compressed, each of radiometer antennas 620U of the upper array is in direct contact with one side of the patient's breast and each of radiometer antennas 620L of the lower array 620L is in direct contact with the opposite side of the patient's breast.

Equipment 606 may include scanning means of varying complexity for controlling the coupling of the outputs of the respective radiometer antennas 620U and 620L of the upper and lower arrays through cables 604U and 604L as an input to the radiometer of equipment 606. In its simplest form, the scanning means forwards the microwave noise output of each radiometer antenna of one of the arrays, in turn, as the radiometer input and then forwards the microwave noise output of each radiometer antenna of the other of the arrays, in turn, as the radiometer input. In a more complex form which provides depth information, the scanning means may employ known difference-in-time-of-arrival techniques in forwarding a microwave noise signal derived from the microwave noise outputs of each pair of opposite corresponding radiometer antennas of the upper and lower arrays, in turn, as the radiometer input. In a still more complex form, the scanning means may employ computer axial tomography techniques in scanning the radiometer antennas and deriving, in turn, microwave noise signal inputs to the radiometer from which the 3-dimensional position of the cancer lesion within the breast can be ascertained.

The cooperative combination of the radiometric equipment with mammograph equipment 600 has two advantages. First, the correspondence in the location within the breast of the spatial position of the cancerous lesion is insured because the lightly compressed breast remains immobile during the occurrence of both procedures. Second, since both procedures take place at the same time, both procedures at different times, the breast need be compressed only once, rather than twice. This halves the chance of metastasis from a cancerous lesion occurring.

What is claimed is:

1. In a radiometer for determining the temperature $T_s$ of a specimen in which the temperature $T_s$ is never higher than a certain maximum temperature; wherein microwave noise power emitted by said specimen is applied as an input to said radiometer for a first given time $t_s$ and microwave noise power derived from a reference noise source is applied as an input to said radiometer for a second given time $t_r$, and a feedback output from said radiometer is employed to minimize the difference between respective microwave noise energies emitted by said specimen and derived from said reference noise source that are applied as inputs to said radiometer; the improvement comprising:

first means for deriving an amount of said microwave noise power from said reference noise source applied as a radiometer input that corresponds to a temperature $T_r$ which is always higher than said certain maximum temperature; and second means responsive to said feedback output for adjusting at least one of $T_r$, $t_r$ and $t_s$ to effect said minimization.

2. The radiometer defined in claim 1, wherein said second means adjusts $t_r$.

3. The radiometer defined in claim 1, wherein said radiometer comprises:

third means including a directional coupler for combining said microwave noise power derived from said reference noise source, that is applied for a first portion of each of successive time cycles by said third means as a first input to said directional coupler, with said microwave noise power emitted by said specimen, that is applied continuously by said third means as a second input to said directional coupler, to derive a single microwave power output from said directional coupler;

fourth means for amplifying said directional-coupler single output;

a synchronous detector;

fifth means including microwave detection means and a calibrated attenuator responsive to said amplified single output from said directional coupler for applying an attenuated first microwave-detected signal as an input to said synchronous detector during said first portion of each of said successive time cycles and applying an unattenuated second microwave-detected signal as an input to said synchronous detector during a remaining portion of each of said successive time cycles; and said second means includes feedback means for adjusting a given one of $T_r$ and $t_r$ in accordance with an output from said synchronous detector.

4. The radiometer defined in claim 3, wherein:

said calibrated attenuator is a 3 db attenuator.

5. The radiometer defined in claim 3, wherein:

said third means includes first switch means having On and Off switch positions through which said microwave noise power derived from said reference noise source is applied as a first input to said directional coupler only when said first switch is in its On switch position;

said fifth means includes SPDT second and third switch means through which said attenuated first microwave-detected signal is applied as an input to said synchronous detector when both said SPDT second and third switch means are in a first switch position thereof, and through which said unattenuated first microwave-detected signal is applied as an input to said synchronous detector when both said SPDT second and third switch means are in a second switch position thereof; and sixth means for switching said first switch means between its On and Off switch positions, said second and third switch means back and forth between their respective first and second switch positions and controlling the operation of said synchronous detector in synchronism with one another.

6. The radiometer defined in claim 5, wherein:

said third means further includes a PIN diode switch which, in its conductive state, applies microwave noise power from said reference noise source to said first SPDT switch for application as said first input to said directional coupler when said first SPDT switch is in its first switch position;

said sixth means includes a square-wave generator that generates said successive time cycles and derives a 50% duty cycle signal of each of said successive time cycles for effecting said switching of said first, second and third switch means back and forth between their respective first and second switch positions and controlling the operation of said synchronous detector; and said feedback means includes a pulse width modulator for adjusting $t_r$ by rendering said PIN diode conductive for the duration of said first portion of each of said successive time cycles in accordance with said output from said synchronous detector, wherein the maximum duration of said first portion is no greater than one-half of each of said successive time cycles.

7. The radiometer defined in claim 6, further comprising:

temperature display means coupled to said pulse width modulator for indicating $T_s$ in correspondence with said duration of said first portion of each of said successive time cycles.

8. The radiometer defined in claim 5, wherein:

said sixth means comprises a variable duty cycle switch driver; and said feedback means includes a null seeking servo responsive to the output of said synchronous detector for adjusting $t_r$ by controlling the duty cycle of said variable duty cycle switch driver.

9. The radiometer defined in claim 8, further comprising:

temperature display means coupled to said variable duty cycle switch drive for indicating $T_s$ in correspondence with the value of the duty cycle derived by said variable duty cycle switch driver.

10. The radiometer defined in claim 5, wherein:

said reference noise source is a diode noise source.

11. The radiometer defined in claim 5, wherein:

said reference noise source is a variable noise source; and said feedback means is coupled to said variable noise source for adjusting $T_r$ by deriving an amount of microwave noise power from variable noise source in accordance with said output from said synchronous detector.

12. The radiometer defined in claim 11, further comprising:

temperature display means coupled to said variable noise source for indicating $T_s$ in correspondence with the amount of microwave noise power from said variable noise source.

13. The radiometer defined in claim 12, wherein said specimen is body tissue and wherein:

said variable noise source includes a matched resistor, a heater that is energized in accordance with said output from said synchronous detector for heating said matched resistor, and a temperature sensing device for sensing the temperature of said heated matched resistor that is coupled to said temperature display means; and said third means includes an amplifier and matched attenuator for deriving said microwave noise power from said heated matched resistor that is applied as a first input to said directional coupler, said amplifier including an On/Off control input operated by said sixth means, whereby said amplifier constitutes said first switch means; and the respective values of said amplifier and matched attenuator being such that said radiometer is provided with a closed-loop gain that results in said matched resistor being heated to a temperature $T_r$ that is substantially equal to the specimen temperature $T_r$.

14. The radiometer defined in claim 13, wherein:

said calibrated attenuator is a 3 db attenuator.

15. The radiometer defined in claim 13, wherein:

said directional coupler is a bi-directional coupler responsive to microwave noise power applied to a third input thereof for compensating for emissivity error in the microwave noise power emitted by said specimen; and a second amplifier matched with said first-mentioned amplifier and a second calibrated attenuator for applying microwave noise power from said heated matched resistor to said third input of said bi-directional coupler.

* * * * *